(12) United States Patent
Garcia et al.

(10) Patent No.: US 11,850,188 B2
(45) Date of Patent: Dec. 26, 2023

(54) CORNEAL LENTICULE EXTRACTION TOOL

(71) Applicant: AMO Development, LLC, Irvine, CA (US)

(72) Inventors: Jose L Garcia, Fremont, CA (US); Trevor Hannon, Hayward, CA (US); Christina Lagarto, Sunnyvale, CA (US)

(73) Assignee: AMO Development, LLC, Irvine, CA (US)

( * ) Notice: Subject to any disclaimer, the term of this patent is extended or adjusted under 35 U.S.C. 154(b) by 146 days.

(21) Appl. No.: 16/372,300

(22) Filed: Apr. 1, 2019

(65) Prior Publication Data

US 2020/0306087 A1 Oct. 1, 2020

(51) Int. Cl.
*A61F 9/013* (2006.01)
(52) U.S. Cl.
CPC ........ *A61F 9/013* (2013.01); *A61B 2217/005* (2013.01)
(58) Field of Classification Search
CPC ............ A61F 9/013; A61F 9/007; A61F 2009/00872; A61F 9/00736; A61F 9/00781; A61B 10/0283; A61B 5/150145; A61B 2017/22079
See application file for complete search history.

(56) References Cited

U.S. PATENT DOCUMENTS

| | | | |
|---|---|---|---|
| 1,386,436 A | 8/1921 | Smith et al. | |
| 1,657,497 A | 1/1928 | Cichon et al. | |
| D272,479 S | 1/1984 | Roeyen et al. | |
| 4,727,876 A | 3/1988 | Porat et al. | |
| D301,279 S | 5/1989 | Amende | |
| 4,955,897 A | 9/1990 | Ship | |
| 5,167,618 A | 12/1992 | Kershner | |
| D341,886 S | 11/1993 | Stolte | |

(Continued)

FOREIGN PATENT DOCUMENTS

| | | |
|---|---|---|
| RU | 2067855 C1 | 10/1996 |
| SU | 316447 A1 | 10/1971 |
| WO | 2017195912 A1 | 11/2017 |

OTHER PUBLICATIONS

International Search Report and Written Opinion for Application No. PCTIB2020052635, dated Jun. 3, 2020, 7 pages.

*Primary Examiner* — Kelly J Bekker
*Assistant Examiner* — Mohammed S Adam
(74) *Attorney, Agent, or Firm* — Johnson & Johnson Surgical Vision, Inc.

(57) ABSTRACT

Improved corneal lenticule extraction tools which integrate defined angles, tip features, and the use of vacuum into the tool to aid in the removal of the lenticule. The tool has a body and a tip each with an internal air channel. The tip has a straight portion and a curved portion at a distal end, with one or more orifices disposed on the curved portion. The body either has a mechanism for generating a vacuum in the internal air channel, such as a resilient diaphragm, or is connected to an external vacuum source. Use of tip features and angles helps the surgeon find tissue edges during tissue removal. The use of vacuum aids to draw the tissue to the tool and to hold the tissue by the tool. The improved tools improve speed of extraction as well as completeness of extraction so that no tissue is left behind.

3 Claims, 8 Drawing Sheets

(56) References Cited

U.S. PATENT DOCUMENTS

| | | | |
|---|---|---|---|
| 5,403,307 A * | 4/1995 | Zelman | A61F 9/00736 606/4 |
| 5,569,280 A * | 10/1996 | Kamerling | A61F 9/00754 606/107 |
| 5,630,821 A | 5/1997 | Klaas | |
| 5,653,724 A | 8/1997 | Imonti | |
| 5,755,700 A | 5/1998 | Kritzinger et al. | |
| 5,800,406 A | 9/1998 | Kritzinger et al. | |
| 5,860,985 A | 1/1999 | Anschutz | |
| 6,135,984 A | 10/2000 | Dishler | |
| D436,663 S | 1/2001 | Chandler et al. | |
| 6,273,894 B1 | 8/2001 | Dykes | |
| 6,322,363 B1 | 11/2001 | Beecher et al. | |
| D452,936 S | 1/2002 | Grisoni | |
| 6,413,245 B1 | 7/2002 | Yaacobi et al. | |
| 6,596,000 B2 | 7/2003 | Chan et al. | |
| D490,893 S | 6/2004 | Bogazzi | |
| D490,896 S | 6/2004 | Bogazzi | |
| D493,889 S | 8/2004 | Koo | |
| D517,212 S | 3/2006 | Skarine | |
| 7,153,316 B1 | 12/2006 | Mcdonald | |
| D589,614 S | 3/2009 | Cook | |
| D616,540 S | 5/2010 | Brigatti et al. | |
| D642,266 S | 7/2011 | Marsteller et al. | |
| 8,162,953 B2 | 4/2012 | Dishler et al. | |
| 8,398,578 B1 * | 3/2013 | Zolli | A61F 9/00736 604/19 |
| 8,469,948 B2 | 6/2013 | Dishler et al. | |
| D690,419 S | 9/2013 | Porat | |
| 8,657,851 B2 | 2/2014 | Aufaure et al. | |
| D716,498 S | 10/2014 | Wolff | |
| D738,611 S | 9/2015 | Gupta | |
| D740,416 S | 10/2015 | Dolmetsch | |
| D775,727 S | 1/2017 | Khaw | |
| D783,901 S | 4/2017 | Kim et al. | |
| 9,662,097 B2 * | 5/2017 | Honda | A61B 17/00234 |
| 2002/0116020 A1 | 8/2002 | Kurenkov | |
| 2003/0135221 A1 * | 7/2003 | Sabet | A61F 9/007 606/107 |
| 2003/0167033 A1 | 9/2003 | Chen et al. | |
| 2004/0073231 A1 | 4/2004 | Juan et al. | |
| 2006/0173404 A1 * | 8/2006 | Urich | A61M 1/0058 604/35 |
| 2009/0240281 A1 | 9/2009 | Andre | |
| 2011/0135626 A1 | 6/2011 | Kovalcheck | |
| 2011/0172675 A1 | 7/2011 | Danta et al. | |
| 2013/0226152 A1 * | 8/2013 | Zolli | A61F 9/00825 604/540 |
| 2013/0281993 A1 | 10/2013 | Dishler et al. | |
| 2014/0058425 A1 | 2/2014 | Porat | |
| 2014/0236163 A1 * | 8/2014 | Olson | A61F 2/1662 606/107 |
| 2015/0257928 A1 * | 9/2015 | Iseli | A61F 9/0017 604/93.01 |
| 2015/0313755 A1 * | 11/2015 | Schaller | A61F 9/007 606/107 |
| 2016/0074220 A1 | 3/2016 | Ianchulev et al. | |
| 2017/0128263 A1 | 5/2017 | Maminishkis | |
| 2017/0238956 A1 | 8/2017 | Dam-Huisman et al. | |
| 2018/0296391 A1 | 10/2018 | Charles et al. | |
| 2020/0138628 A1 * | 5/2020 | Kahook | A61F 9/00781 |
| 2020/0188561 A1 * | 6/2020 | Grueebler | A61M 1/85 |

* cited by examiner

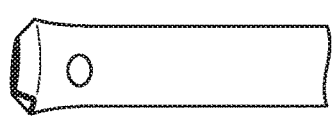
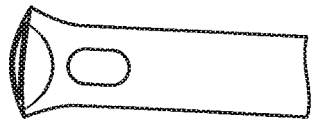
FIG. 3A          FIG. 3B          FIG. 3C
FIG. 3D
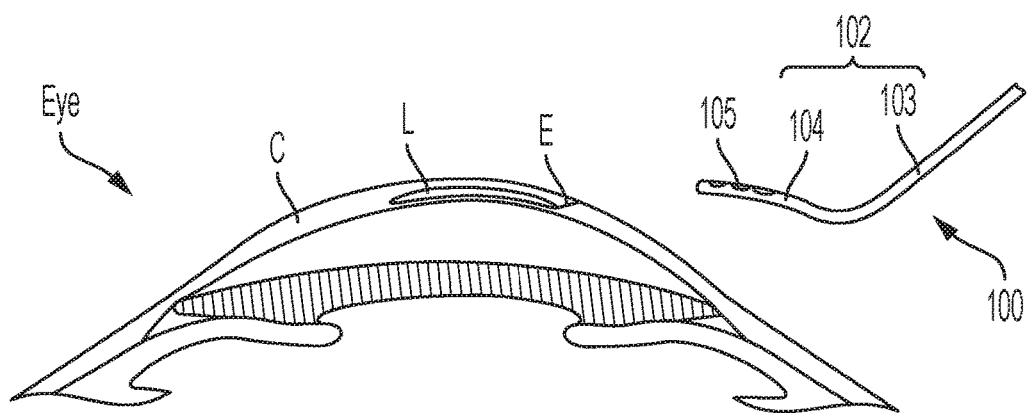
FIG. 4

CORNEAL LENTICULE EXTRACTION TOOL

BACKGROUND OF THE INVENTION

Field of the Invention

This invention relates to a tool for extracting a lenticular tissue from a cornea to achieve vision correction.

Description of Related Art

Eye surgery has become commonplace with some patients pursuing it as an elective procedure to avoid using contact lenses or glasses to correct refractive problems, and others pursuing it to correct adverse conditions such as cataracts. And, with recent developments in laser technology, laser surgery is becoming the technique of choice for ophthalmic procedures. Different laser eye surgical systems use different types of laser beams for the various procedures and indications. These include, for instance, ultraviolet lasers, infrared lasers, and near-infrared, ultra-short pulsed lasers. Ultra-short pulsed lasers emit radiation with pulse durations as short as 10 femtoseconds and as long as 3 nanoseconds, and a wavelength between 300 nm and 3000 nm.

Prior surgical approaches for reshaping the cornea include laser assisted in situ keratomileusis (hereinafter "LASIK"), photorefractive keratectomy (hereinafter "PRK") and Small Incision Lenticule Extraction (hereinafter "SMILE"). In the SMILE procedure, instead of ablating corneal tissue with an excimer laser following the creation of a corneal flap, the technique involves tissue removal with two femtosecond laser incisions that intersect to create a lenticule for extraction. The extraction of the lenticule changes the shape of the cornea and its optical power to accomplish vision correction. Lenticular extractions can be performed either with or without the creation of a corneal flap. With the flapless procedure, a refractive lenticule is created in the intact portion of the anterior cornea and removed through a small incision.

In a corneal lenticule extraction procedure, the lenticule is formed by cutting a top lenticule surface and a bottom lenticule surface in the cornea, where the two lenticule surfaces intersect each other at their peripheral edges to form an isolated volume of the cornea in between, i.e. the corneal lenticule. An entry cut, which extends from the anterior cornea surface to the top or bottom lenticule surface or the lenticule edge, is formed to provide access for extraction tools and passage for lenticule removal.

SUMMARY

Extraction of the lenticular tissue can be difficult. The lenticule corneal tissue tends to easily detach from the bottom cut, but the tissue tends to bias upward in the cut and it can be difficult to define the tissue edge to aid in removal. Surgeons may use standard surgical tweezers to remove the lenticule, but at times may encounter difficulty during removal.

Accordingly, the present invention is directed to a corneal lenticule extraction tool that substantially obviates one or more of the problems due to limitations and disadvantages of the related art.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve the above objects, the present invention provides a tool for removing a lenticule tissue from a cornea of a patient, which includes: an elongated body having an internal air channel; and an elongated tip extending from the body and having an internal air channel in air communication with the air channel of the body, wherein the tip has a straight portion which extends from the body and a curved portion at a distal end of the tip, an orientation of the curved portion and an orientation of the straight portion forming an angle between 120 to 150 degrees, and wherein the tip has one or more orifices disposed on a side of the curved portion, the orifices facing a direction that lies within a plane that contains the curved portion and the straight portion, the curved portion being free of any orifices that face a direction perpendicular to the plane that contains the curved portion and the straight portion.

In another aspect, the present invention provides a tool for removing a lenticule tissue from a cornea of a patient, which includes: an elongated body, the body having an internal air channel and a mechanism for generating a negative pressure in the internal air channel, the mechanism including a flexible and resilient diaphragm on the body; and an elongated tip extending from the body and having an internal air channel in air communication with the air channel of the body, wherein the tip has a straight portion which extends from the body and a curved portion at a distal end of the tip, an orientation of the curved portion and an orientation of the straight portion forming an angle between 120 to 150 degrees, and wherein the tip has one or more orifices disposed on a side of the curved portion and in air communication with the internal air channel of the tip, the orifices facing a direction that lies within a plane that contains the curved portion and the straight portion.

In yet another aspect, the present invention provides a tool for removing a lenticule tissue from a cornea of a patient, which includes: an elongated body having an internal air channel; an elongated tip extending from the body and having an internal air channel in air communication with the air channel of the body, wherein the tip has a first portion which extends from the body and a second portion at a distal end of the tip, an orientation of the second portion and an orientation of the first portion forming an angle between 120 to 150 degrees, and wherein the second portion of the tip has one or more orifices in air communication with the internal air channel of the tip; and one or more flexible skirts each disposed around one of the orifices.

In yet another aspect, the present invention provides a tool for removing a lenticule tissue from a cornea of a patient, which includes: an elongated body having an internal air channel; and an elongated tip extending from the body and having an internal air channel in air communication with the air channel of the body, wherein the tip has a first portion which extends from the body and a second portion at a distal end of the tip, an orientation of the second portion and an orientation of the first portion forming an angle between 120 to 150 degrees, wherein the second portion of the tip include one or more orifices in air communication with the internal air channel of the tip, and an obstruction inside the orifice, the obstruction including one or more of: a rib, a cross, a mesh, and a disk with slits.

It is to be understood that both the foregoing general description and the following detailed description are exemplary and explanatory and are intended to provide further explanation of the invention as claimed.

BRIEF DESCRIPTION OF THE DRAWINGS

FIGS. 3A-3D illustrate various shapes of the orifice in the tip of the vacuum pen of the first embodiment.

FIG. 4 schematically illustrates the eye including the lenticule formed in the cornea, and the tip of the vacuum pen of the first embodiment.

DETAILED DESCRIPTION OF PREFERRED EMBODIMENTS

Embodiments of the present invention provide various improved corneal lenticule extraction tools by integrating defined angles, tip features, and/or use of vacuum into a tool to aid in the removal of the lenticule. Use of tip features and angles helps the surgeon find tissue edges during tissue removal. The use of vacuum also aids to draw the tissue to the tool and to hold the tissue by the tool. The improved tools improve speed of extraction as well as completeness of extraction so that no tissue is left behind.

Figure 1A:
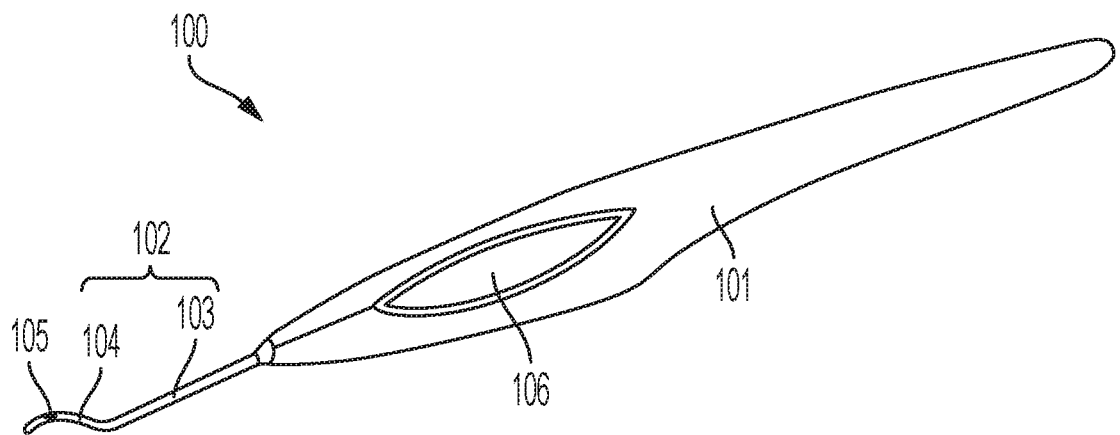
FIGS. 1A-1F illustrate a vacuum pen for lenticule extraction according to a first embodiment of the present invention and its variations.

A first embodiment of the present invention provides a lenticule extraction tool in the form of a vacuum pen with a rigid tip, which uses vacuum (i.e. negative pressure) to provide the means of holding the lenticule during extraction. As shown in FIG. 1A, the vacuum pen 100 has an elongated body (or handle) 101 and an elongated tip 102 joined to the body. The body is designed to be held in a surgeon's hand as if holding a pen, and preferably has an ergonomic shape that fits the hand.

The tip 102 is hollow inside, forming an air channel. For example, the tip may be formed of a rigid tube with a substantially round cross section. The tip may have a size of, for example, 16-25 gauge, and more preferably, 19-22 gauge. One or more orifices 105 are formed on the side wall of the tip 102 near its distal end, and are in air communication with the internal air channel. The air channel inside the tip 102 is connected to and in air communication with an air channel inside the body 101, which is in turn connected to and in air communication with a vacuum source. The one or more orifices 105 may form a row along the length of the tip, multiple rows, etc. For example, the variations shown in FIGS. 1B-1C have two (105B), and three (105C) orifices, respectively, forming a row. The distal end of the tip is preferably closed.

The tip 102 includes a substantially straight portion 103 which extends from the body 101, and a curved portion 104 at the distal end, where the orifices are formed along the curved portion. The curved portion 104 is bent relative to the straight portion 103, i.e., the general orientation of the curved portion, represented by an imaginary straight line that connects the distal end point of the tip and the approximate point where the straight portion ends and the curved portion starts, forms a non-zero angle relative to the general orientation of the straight portion. The angle is preferably 120 to 150 degrees. The direction that the curved portion 104 bends toward is referred to as the "up" direction. In some embodiments, the curved portion 104 is convex toward the "up" direction, and preferably has a curvature of approximately 7.5 mm radius, which corresponds to approximately the 95th percentile of corneal curvature.

In some embodiments, the orifices are located only on the "up" side of the curved portion 104, and the vacuum pen 100 is used for corneal lenticule extraction in a posterior approach, i.e., the curved part of the tip is inserted below the lenticule, between the bottom lenticular surface and the posterior surface of the cornea. Thus, the orifices on the "up" side of the curved portion face the bottom surface of the lenticule (see FIG. 4). When a vacuum is applied to the internal channels of the vacuum pen, a suction force is generated at the orifices to hold the lenticule from the bottom.

In other embodiments (not shown), the orifices are located only on the "down" side of the curved portion 104, and the vacuum pen 100 is used for corneal lenticule extraction in an anterior approach, i.e., the curved part of the tip is inserted above the lenticule, between the top lenticular surface and the anterior surface of the cornea. The orifices on the "down" side of the curved portion 104 thus face the top surface of the lenticule to hold the lenticule from the top.

Note that with either up-facing or down-facing orifices, no orifice is provided that faces the "side" of the tip, i.e., facing a direction perpendicular to a plane that contains the curved portion 104 and the straight portion 103. This is because the side part of the curved portion 104 will not contact either lenticule surface during extraction, and orifices located in that part will not be useful and may even be detrimental.

FIG. 4 illustrates the eye, the cornea C, the lenticule L formed in the cornea, the entry cut E, and the tip 102 of the vacuum pen 100. As mentioned earlier, the angle between the curved portion 104 and the straight portion 103 is preferably about 120 to 150 degrees; thus, when the curved portion is inserted into the cornea, the angle of the straight portion 103 (and hence the body 101) is about 30 to 60 degrees relative to the optical axis of the eye. More preferably, the angle is about 45 degrees.

The tip 102 may be made of metal, plastic, or other suitable rigid materials. The tip may be formed of a metal or plastic tube of a desired diameter and thickness, for example, 16-25 gauge, and more preferably, 19-22 gauge. The tip 102 preferably has a round cross-sectional shape, but it may also have a flattened shape. The shape of the orifice may be round (FIG. 3A, e.g., 0.3 mm diameter), oval (FIG. 3B, e.g., 0.5 mm length and 0.3 mm width), rectangle with two semicircular ends (FIG. 3C, e.g., 0.6 mm length and 0.3 mm width), key slot (FIG. 3D, e.g., 1 mm length and 0.3 mm to 0.6 mm width), or other suitable shapes. More generally, the dimensions of the orifices may be from 0.2 to 0.8 mm. Preferably, the total area of the one or more orifices is greater than the cross-sectional area of the internal channel of the tip 102 to provide optimal suction force.

The body 101 of the vacuum pen 100 may be made of plastic or other suitable materials, and may have any suitable shape. Some examples of alternative shapes of the body are shown in FIGS. 1B-1F (handles 101B-101F).

Figure 1B:
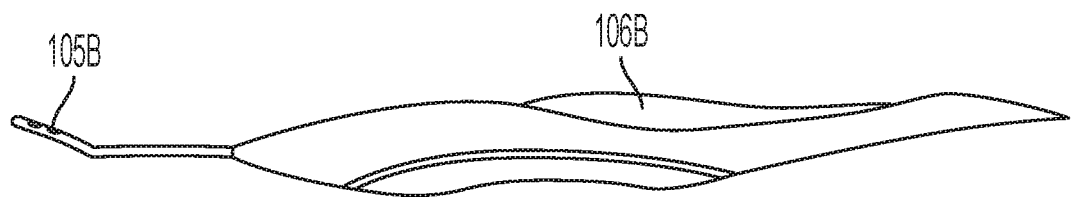
Figure 1C:
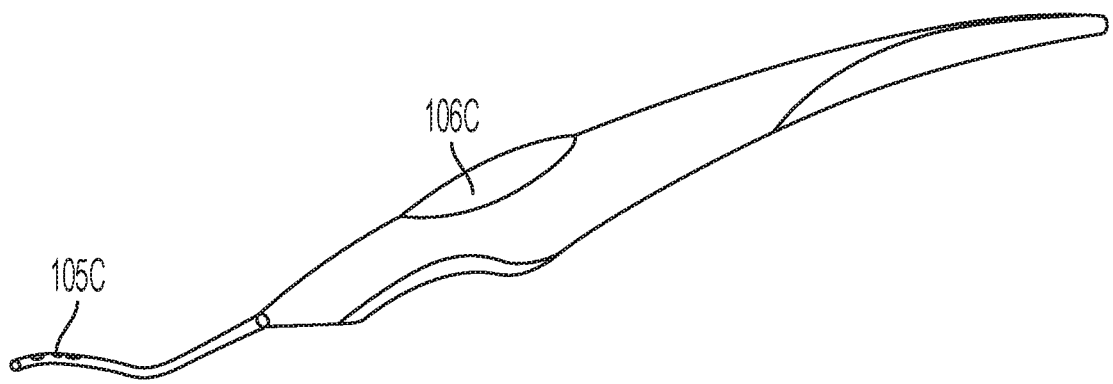
Figure 1D:
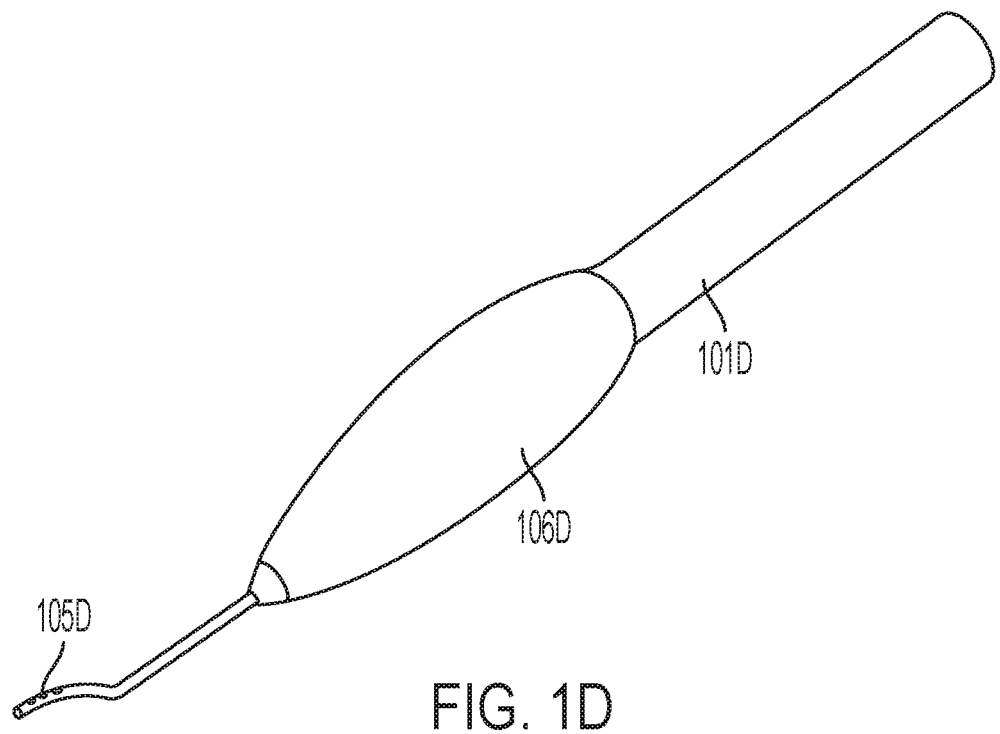
Figure 1E:
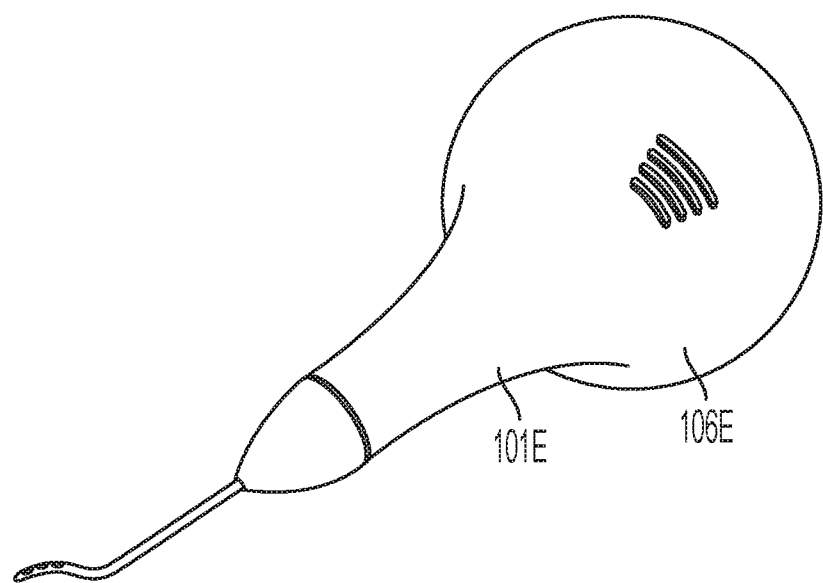

In some embodiments, the vacuum source that generates the suction force at the orifices is a manual mechanical structure such as a rubber squeeze bulb or other forms of a squeeze chamber for generating a vacuum, and is a part of the body 101. In the embodiment shown in FIG. 1A, for example, the body 101 has an internal chamber with a flexible and resilient (e.g. name of rubber, polytetrafluoroethylene (PTFE), etc.) diaphragm 106 exposed to the exterior of the body. The diaphragm may be manually squeezed and released (so that it returns to a fully expanded shape due to the resilience in the material) by the surgeon while holding the vacuum pen to generate a vacuum. FIGS. 1B-1D show alternative embodiments where the bodies incorporate squeeze chambers with diaphragms 106B-106D having different locations and configurations on the body 101. FIG. 1E shows an embodiment where the body 101E is mainly constituted by a rubber bulb 106E that functions as the vacuum source.

Figure 2A:
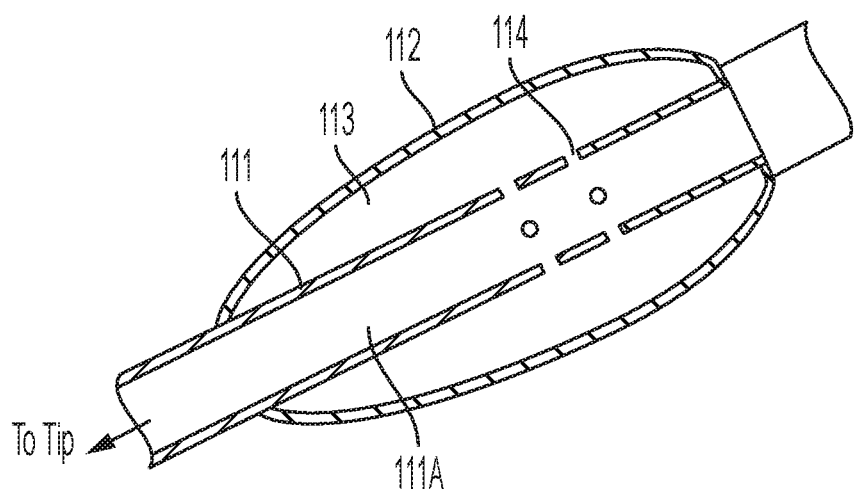
FIGS. 2A-2B illustrates examples of a manual mechanical vacuum source of the vacuum pen according to embodiments of the present invention.

FIG. 2A illustrates the structure of a manual mechanical vacuum source, for example, similar to that shown in FIG. 1D. The body of the vacuum pen has an internal channel 111A and a flexible (e.g. rubber, PTFE) bulb 112 disposed around the internal channel. A space 113 formed between the bulb 112 and the wall 111 of the channel 111A is in air communication with the internal channel 111A via orifices 114 or other forms of openings. Squeezing and then releasing the bulb 112 generates a vacuum in the internal channel 111A which is transmitted to the internal air channel of the tip of the vacuum pen.

Figure 2B:
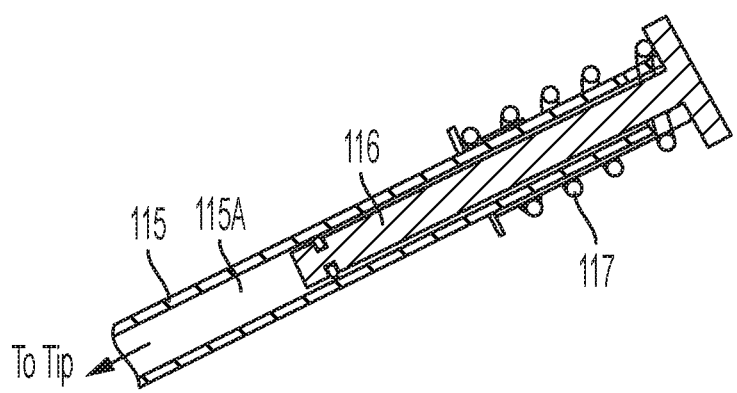

FIG. 2B illustrates the structure of another manual mechanical vacuum source. The body 115 of the vacuum pen is a tube defining a cylindrical internal chamber 115A; a plunger 116 is disposed inside the chamber. The plunger 116 is biased in an outward direction by a spring 117 or other resilient member. Pushing the plunger 116 in against the biasing force and then releasing it generates a vacuum in the internal chamber which is transmitted to the channel inside the tip of the vacuum pen (not shown).

In some other embodiments, the vacuum source that generates the suction force at the orifices is an external vacuum pump. The vacuum levels of the pump may be, for example, approximately 50 mmHg to 720 mmHg. For example, in the embodiment shown in FIG. 1F, the proximal end of the body 101F has a port 107F configured to be connected to an external vacuum pump via a tube.

Figure 1F:
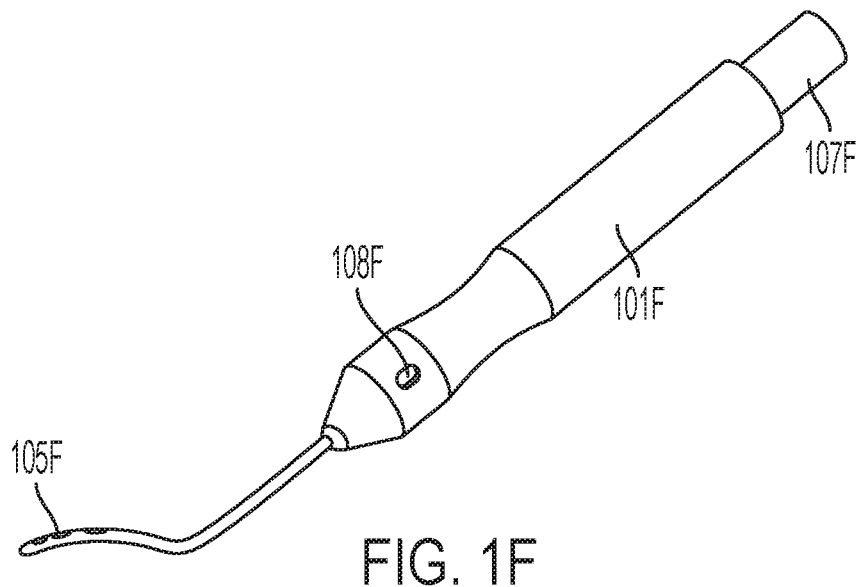

In the embodiment that employs an external vacuum pump, as shown in FIG. 1F, an orifice 108F is formed on the body 101F and in air communication with the air channel within the body. While holding the body, the surgeon may use his finger to block or unblock, or partially block, the orifice 108F to regulate the level of vacuum in the internal air channel. Thus, this orifice 108F acts as an On/Off port for the vacuum force. When the On/Off port is open (unblocked), the air can flow freely into the internal air channel, so that when the tool tip contacts the lenticule, vacuum at the lenticule surface is not achieved due to the air inflow through the On/Off port. When the On/Off port is closed (blocked), and the tip contacts the lenticule, a vacuum is achieved to hold the lenticule tissue and allows for removal of the lenticule. This On/Off port allows the surgeon to quickly toggle between vacuum On and Off at the tip.

Figure 5A:
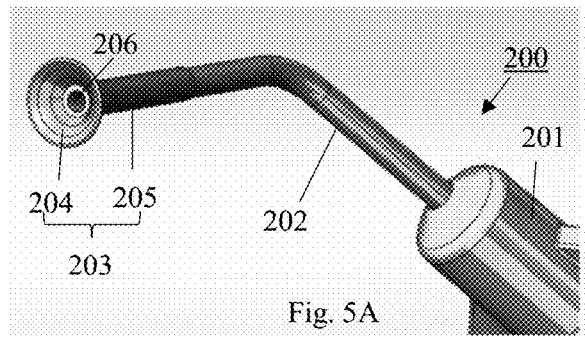
FIGS. 5A-5F illustrate examples of the tip of a vacuum pen for lenticule extraction according to a second embodiment of the present invention and its variations.

A second embodiment of the present invention is a variation of the vacuum pen of the first embodiment, where instead of the orifices along the distal section of the tip, a flexible end piece is attached to the rigid tip of the vacuum pen to provide a contact surface for holding the tissue. As shown in FIG. 5A, the vacuum pen 200 includes an elongated tip 202 and a flexible end piece 203 attached to the distal end of the tip 202. The tip 202 is a rigid tube attached to a part of the body (handle) 201. The flexible end piece 203 may be formed of rubber, nylon, silicone, PTFE, or other suitable materials. The flexible end piece 203 includes a flexible and conformable skirt 204 that provides the contact surface, and a sleeve portion 205 that fits over a distal section of the tip 202.

The flexible skirt 204 is disposed around an orifice of the tip 202, and functions to increase the surface area that contacts the lenticule and to better conform to the shape of the lenticule, which can increase the effectiveness of the vacuum force generated by the orifice and more securely hold the lenticule.

The vacuum pen may be used to hold the lenticule at various desired locations, such as near the center of the top or bottom lenticule surface, at an off-centered position of the top or bottom lenticule surface, at the edge of the lenticule, etc. To this end, the flexible skirt 204 may be provided in a variety of pre-formed shapes that allows for the best fit and seal to the lenticule. For example, the flexible skirt may have a cone or cup shape (204 in FIG. 5A and 204D in FIG. 5D), an off-centered cone or cup shape (204B in FIG. 5B), a part of a half cylinder (204C in FIG. 5C), multiple cups (204E in FIG. 5E), an elongated bowl shape (204F in FIG. 5F), etc. FIGS. 6A-6E show further examples of possible shapes of the flexible skirt.

In the embodiment of FIG. 5A, the flexible skirt 204 is disposed around the open distal end (orifice) 206 of the tip (rigid tube) 202, and the contact surface of the flexible skirt 204 is generally perpendicular to the longitudinal direction of the distal section of the tip 202. In some other embodiments, the tip (rigid tube) 202 has an orifice located on its side wall, and flexible skirt 204 is located around the orifice, and is contact surface is generally parallel to the longitudinal direction of the distal section of the tip (see e.g. FIGS. 5D, 5E). Moreover, the tip 202 itself may also have a variety of shapes as desired, as shown in FIGS. 5A-5F. For example, similar to the first embodiment, the tip may have a first portion extending from the body, and a second portion that forms an angle of about 120-150 degrees with the first portion. These configurations of the flexible skirt and the tip allow the surgeon to hold the vacuum pen and to more easily place the flexible skirt at desired locations of the lenticule to perform extraction.

Figure 7:
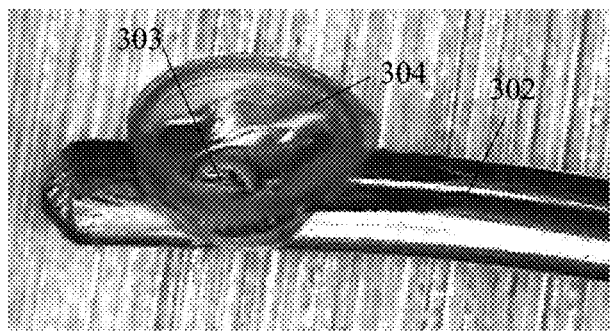
FIG. 7 illustrates an example of the tip of a vacuum pen according to an alternative embodiment of the present invention.

In a vacuum pen according to an alternative embodiment, shown in FIG. 7, a flexible skirt 304 is directly attached to the side of the tip (rigid tube) 302 around an orifice 303 located on the side of the tip. The distal end of the tube 302 is closed. This embodiment is similar to that shown in FIG. 5D in terms of the position and configuration of the flexible skirt but the means of attaching the skirt to the tube are different. This embodiment is also similar to that shown in FIGS. 1A-1F in that one or more orifices are provided on the side of the tip, but with the addition of the flexible skirt around the orifice. The body of the vacuum pen is not shown in FIG. 7.

Figure 8:
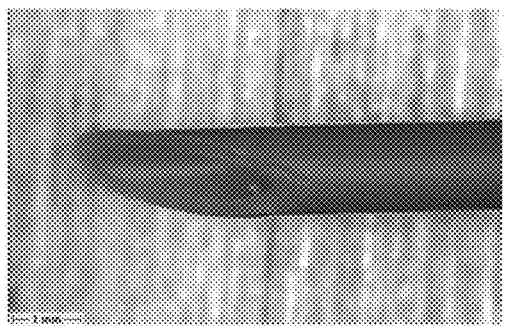
FIG. 8 illustrates an example of the tip of a vacuum pen according to an alternative embodiment of the present invention.

In yet another embodiment, shown in FIG. 8, the tip of the vacuum pen may simply be a somewhat flexible tube, e.g., made of PTFE, with a beveled (elliptical) opening at its end. The bevel angle may be, for example, 15° to 75° angle. This changes the cross-section of the opening from a circle to an oval to increase the surface area in contact with the lenticule.

Figure 9A:
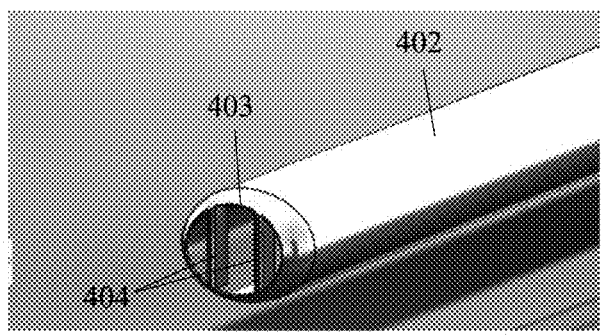
FIGS. 9A-9B illustrate examples of the tip of a vacuum pen with a lenticule aspiration prevention structure according to a third embodiment of the present invention.

A third embodiment of the present invention is a variation of the vacuum pen of the first and second embodiments. As shown in FIG. 9A, instead of the orifices along the side of the tip as in the first embodiment, the distal end of the tip (rigid tube) 402 is open and forms an orifice 403 which functions to communicate the vacuum force and to hold the lenticule tissue. Unlike in the second embodiment, here, no flexible end piece or flexible skirt is provided. The plane of the opening 403 may be perpendicular to the longitudinal direction of the distal section of the tip 402, in which case the opening 403 is a round circle, or non-perpendicular to the longitudinal direction, in which case the opening is an oval shape.

Figure 9B:
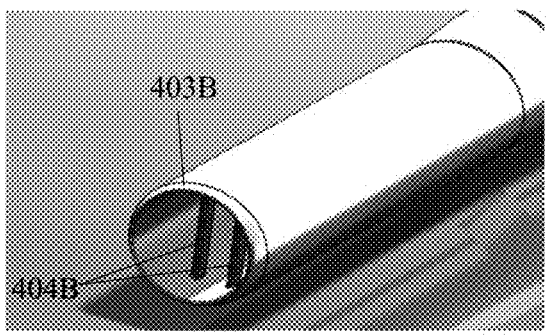

In the third embodiment, a lenticule aspiration prevention structure is provided in the vacuum tip inside the opening 403 to prevent the lenticule from being aspirated up into the vacuum tip and into the vacuum pen. The lenticule aspiration prevention structure is an obstruction, such as one or more ribs 404 positioned across the internal channel of the tip 402, or other structures (not shown) such as a cross, a mesh, a disk with slits, etc. The obstruction may be flush with the opening (FIG. 9A), or slightly recessed back from the opening (FIG. 9B, ribs 404B).

Figure 10:
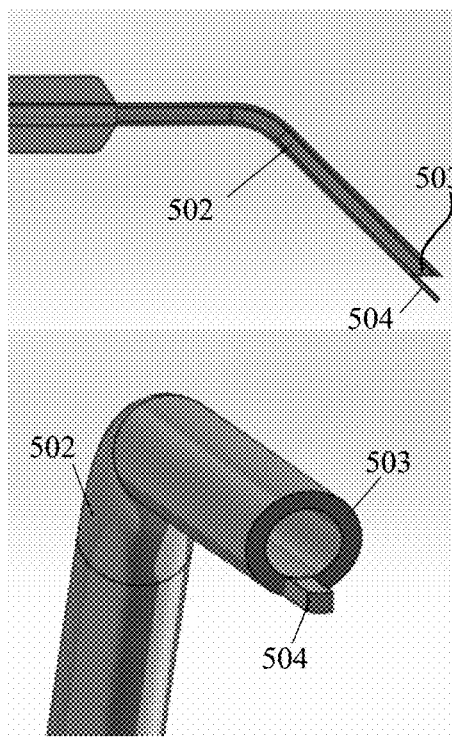
FIG. 10 illustrates a method of forming a lenticule aspiration prevention structure for a vacuum pen of the third embodiment.
Figure 10:
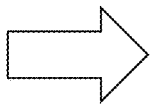
Figure 10:
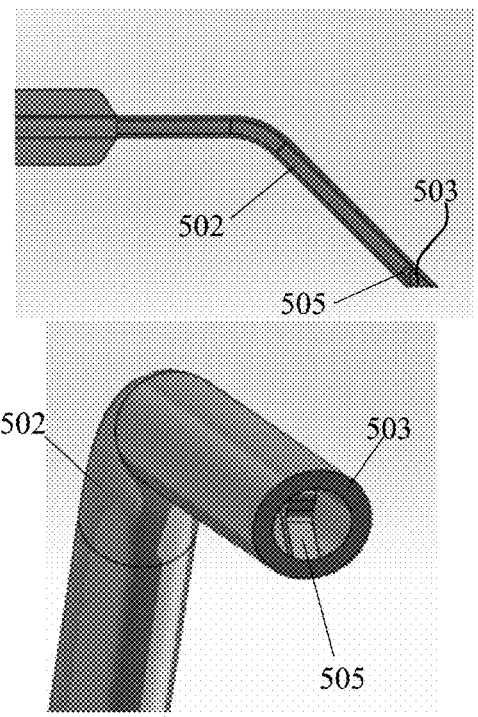

The ribs in the internal channel of the tip may be manufactured in a variety of methods. In one embodiment, shown in FIG. 10, the distal end of the tip (tube) 502 is processed (e.g. by machining or laser cutting) to form an opening 503 and an elongated tab 504, the tab being a part of the original tube wall and protruding longitudinally from the rim of the opening 503 (FIG. 10, left hand side). Then, the tab 504 is bent and compressed toward the opening 503 and the interior of the tip 502 to form a rib 505 inside the tube (FIG. 10, right hand side). The length of the tab 504 is sufficient to form the rib 505 that extends across the interior channel of the tube. In the illustrated embodiment, the rib 505 has a bent shape, which can be formed when the tab 504 is longer than the diameter of the interior channel and the center of the tab is pressed in.

Figure 11:
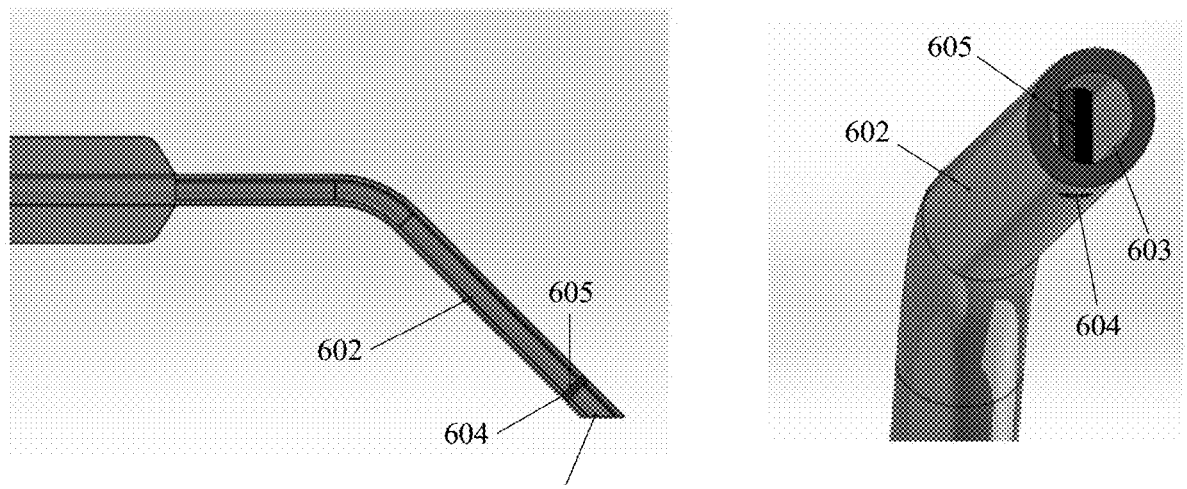
FIG. 11 illustrates another method of forming a lenticule aspiration prevention structure for a vacuum pen of the third embodiment.

In another embodiment, shown in FIG. 11, the rib is formed by drilling a pair of holes 604 through the diameter of the tube (tip) 602, near the end opening 603 of the tube, and affixing (e.g. by welding) a crossbar 605 through the holes across the tip.

Figure 12:
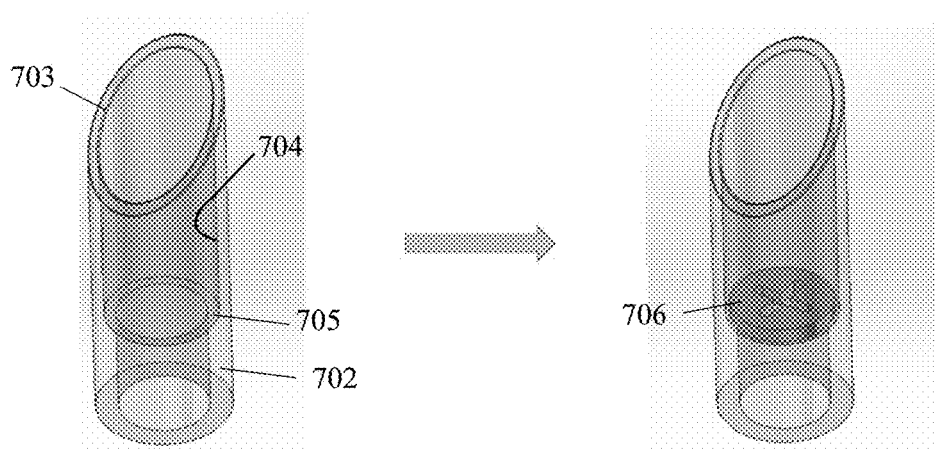
FIG. 12 illustrates another example the lenticule aspiration prevention structure for a vacuum pen of the third embodiment.

In yet another embodiment, shown in FIG. 12, a round disk with slots is used as the obstruction (the lenticule aspiration prevention structure). A counterbore 704 is made at the distal end 703 of the tip (tube) 702, forming a ring shaped step 705 in the tube. A disk 706 with slits (e.g. cross slits, parallel slits, etc.), formed for example by laser cutting, is placed in the counterbore against the step 705, and affixed to the tube, for example by laser welding. Alternatively (not shown), the obstruction is a disk with slits, having the same size as the outer diameter of the tip, affixed (e.g. by laser welding) to the opening of the distal end of the tip.

In yet another embodiment, the entire tip including the lenticule aspiration prevention structure is produced by 3D printing. Any desired shape of the lenticule aspiration prevention structure may be formed by this method.

Figure 5B:
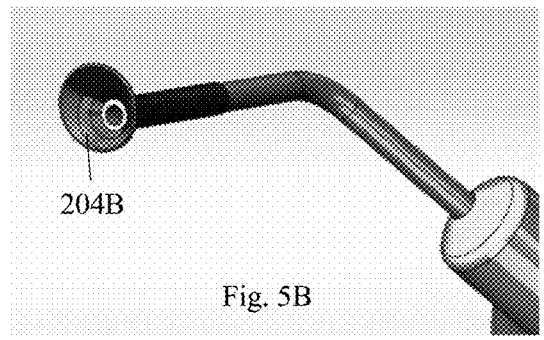
Figure 5C:
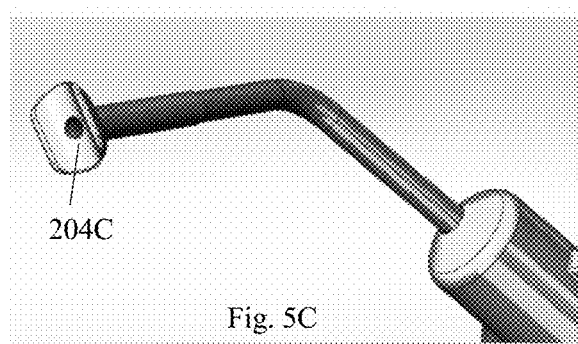
Figure 5D:
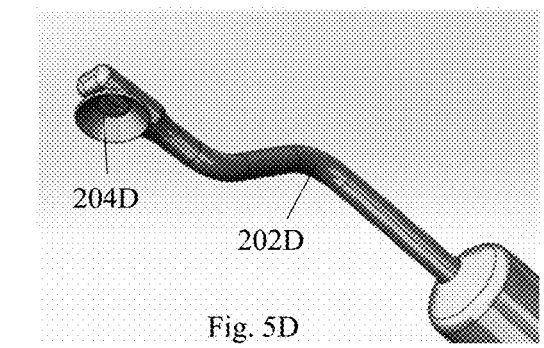
Figure 5E:
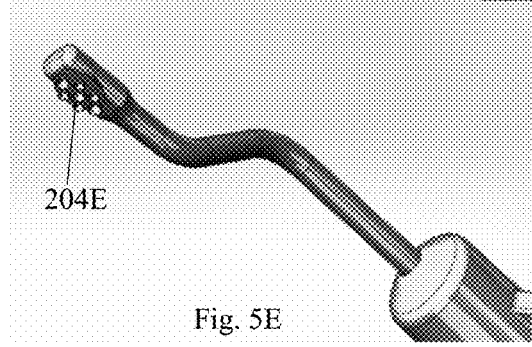
Figure 5F:
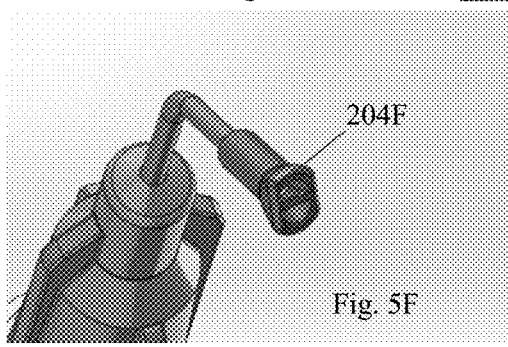
Figure 6A:
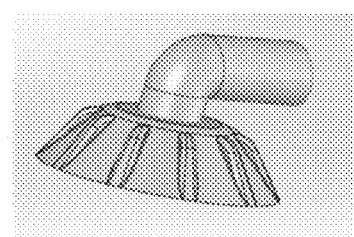
FIGS. 6A-6E illustrate further examples of the flexible skirt of the vacuum pen in the second embodiment.
Figure 6B:
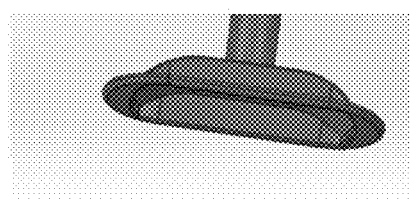
Figure 6C:
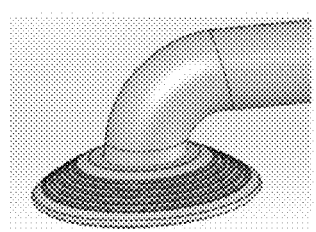
Figure 6D:
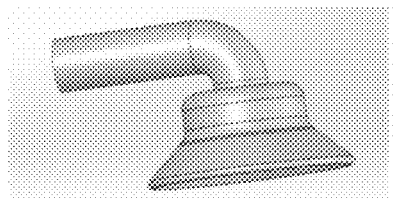
Figure 6E:
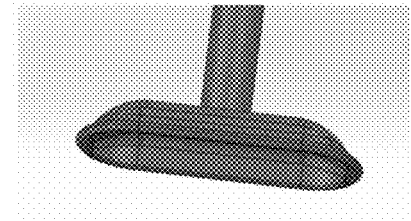

The lenticule aspiration prevention structure described above may also be provided in vacuum pens of the second embodiment, such as those shown in FIGS. 5A, 5B and 5C where the opening of the end of the tip is exposed by the flexible skirt 204/204B/204C. Alternatively, the flexible end piece 203 may include an aspiration prevention structure, formed of the same material as the flexible skirt, disposed over the opening of the end of the tip or near the opening of the flexible end piece (see FIG. 5F).

Figure 13A:
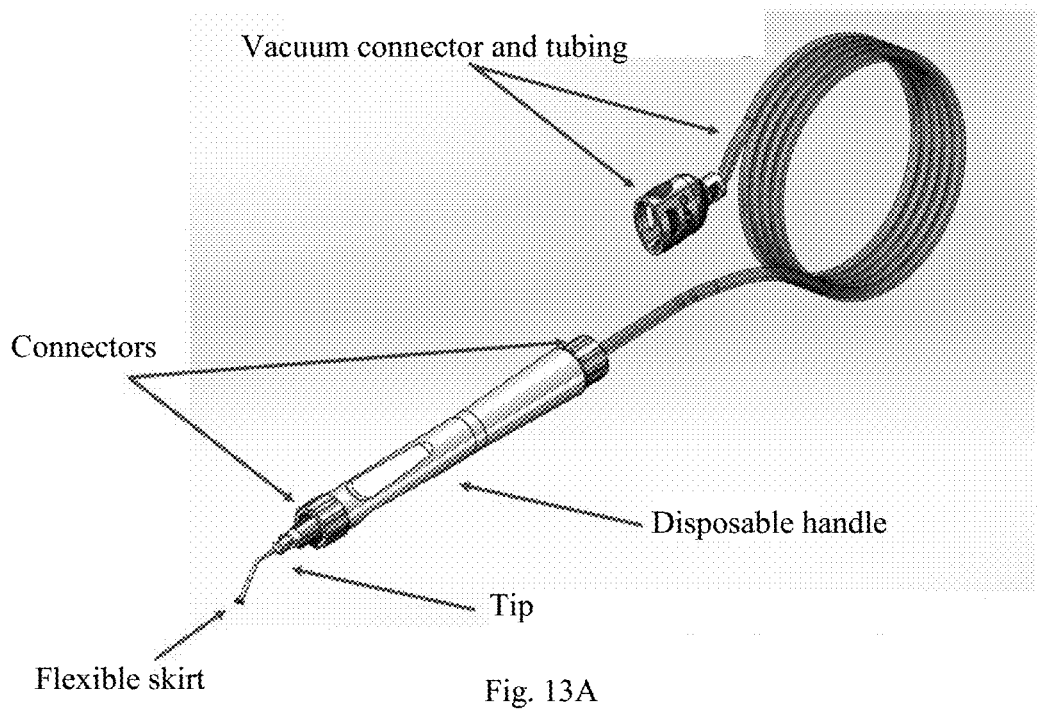
FIGS. 13A-13B illustrate a corneal lenticule extraction system using a vacuum pen with a disposable handle according to another embodiment of the present invention.
Figure 13B:
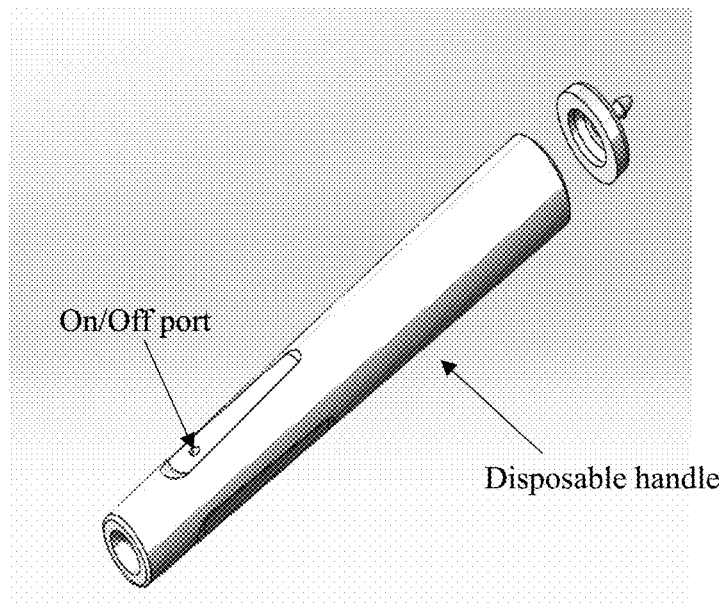

As mentioned earlier, the vacuum source that generates the suction force at the orifices may be provided by an external vacuum pump. In some embodiments, the vacuum pen uses a disposable or single-use handle (body) manufactured out of plastic, configured to be connected to a vacuum pump via a tubing. The handle may be integrated with a single tip, or has a connector so that a variety of alternative tips can be attached to the handle for single use. An example of a vacuum pen system using a disposable handle is shown in FIGS. 13A (system) and 13B (disposable handle). Note that in the embodiment shown in FIG. 13B, the handle has an On/Off port which functions to regulate the vacuum pressure at the tip, in the manner described earlier in connection with FIG. 1F.

Various extraction techniques can be used in conjunction with the various tip designs to perform lenticule extraction. In some embodiments, the eye is flushed with a balanced saline solution (BSS), by inserting BSS into the entry cut, to free the lenticule; the tip of the lenticule extraction tool then can be inserted to remove the lenticule. In some other embodiments, the eye is be flushed with air using the same method as the BSS.

In addition to corneal lenticule extraction, the various tools described above may be used to remove fragmented lens pieces in cataract surgeries.

It will be apparent to those skilled in the art that various modification and variations can be made in the corneal lenticule extraction tool and related methods of the present invention without departing from the spirit or scope of the invention. Thus, it is intended that the present invention cover modifications and variations that come within the scope of the appended claims and their equivalents.

What is claimed is:

1. A tool for removing a lenticule tissue from a cornea of a patient, comprising:
   an elongated body having an internal air channel;
   an elongated tip extending from the body and having an internal air channel in air communication with the air channel of the body,
   wherein the tip has a first portion which extends from the body and a second portion at a distal end of the tip, an orientation of the second portion and an orientation of the first portion forming an angle between 120 to 150 degrees, and
   wherein the second portion of the tip has one or more orifices in air communication with the internal air channel of the tip; and one or more flexible skirts each respectively disposed around one of the one or more orifices, wherein each flexible skirt has a shape that is an off-centered cone or off-centered cup, or a shape of a part of a half cylinder.

2. The tool of claim 1, wherein the one or more orifices include a single orifice formed by an end opening of the tip.

3. The tool of claim 1, further comprising an obstruction inside at least one of the one or more orifices.

* * * * *